United States Patent
Selinfreund et al.

(10) Patent No.: US 7,344,823 B2
(45) Date of Patent: Mar. 18, 2008

(54) TRANSIENT OPTICAL STATE CHANGE MATERIALS USEFUL IN COPY-PROTECTED COMPACT DISCS

(75) Inventors: Richard H. Selinfreund, Guilford, CT (US); Scott Gerger, Des Moines, IA (US); Rakesh Vig, Durham, CT (US); Junzhong Li, New London, CT (US)

(73) Assignee: Verification Technologies, Inc., Essex, CT (US)

( * ) Notice: Subject to any disclaimer, the term of this patent is extended or adjusted under 35 U.S.C. 154(b) by 0 days.

(21) Appl. No.: 10/672,052

(22) Filed: Sep. 26, 2003

(65) Prior Publication Data

US 2004/0121262 A1 Jun. 24, 2004

(51) Int. Cl.
G11B 7/24 (2006.01)
H04L 9/32 (2006.01)

(52) U.S. Cl. ............... 430/270.15; 430/945; 726/26; 726/2; 428/64.4; 369/53.21; 369/47.12; 369/288

(58) Field of Classification Search ............... 430/19, 430/270.1, 945; 544/35, 37
See application file for complete search history.

(56) References Cited

U.S. PATENT DOCUMENTS

| | | | |
|---|---|---|---|
| 5,815,484 A | | 9/1998 | Smith et al. |
| 6,011,772 A | * | 1/2000 | Rollhaus et al. ............ 369/286 |
| 6,228,440 B1 | | 5/2001 | Dailey et al. |
| 6,589,626 B2 | | 7/2003 | Selinfreund et al. |
| 6,641,886 B1 | | 11/2003 | Bakos et al. |
| 2004/0004922 A1 | * | 1/2004 | Selinfreund et al. ..... 369/53.21 |
| 2004/0121262 A1 | * | 6/2004 | Selinfreund et al. ... 430/270.15 |

FOREIGN PATENT DOCUMENTS

| | | | |
|---|---|---|---|
| JP | 01-228976 | * | 9/1989 |
| JP | 08-122836 | * | 5/1996 |

OTHER PUBLICATIONS

Morrison & Boyd, "Organic Chemistry", pp. 360(1973).*
Cauquil, et al. Bull. Soc. Chim. France (1955), pp. 1061-1075.*
Daneke et al., 'Addition von Nucleophilien an in situ erzeugtes Phenoazathionium -Kation', Leibigs Ann. Chem., vol. 740, pp. 52-62 (1970).*
Saraf et al., Recent advances in the synthesis of phenothiazines, Heterocycles, vol. 26(1) pp. 239-273.*
Chandra et al., Studies on some new phenothiazines, Can. J. Chem., vol. 45, pp. 761-767 (1967).*
Strekowski et al., "A synthetic route to 3-(dialkylamino)phenothiazin-5-ium salts . . . ", J. Heterocyclic Chem., vol. 30(6) pp. 1693-1695 (1993).*
International Search Report, International appl. No. PCT/US03/30897 of Sep. 30, 2004.

* cited by examiner

*Primary Examiner*—Martin Angebranndt
(74) *Attorney, Agent, or Firm*—Kelley Drye & Warren LLP

(57) ABSTRACT

A copy-protected optical medium comprising transient optical state change security materials that demonstrating an optical state change when exposed to the wavelengths of from about 770 nm to about 830 nm.

5 Claims, 1 Drawing Sheet

TRANSIENT OPTICAL STATE CHANGE MATERIALS USEFUL IN COPY-PROTECTED COMPACT DISCS

BACKGROUND OF THE INVENTION

1. Field of the Invention

The present invention generally relates to transient optical state change security materials reactive to wavelengths used in optical disc readers, in particular to wavelengths produced by CD optical readers. Such materials may be used by directed application to optical medium to effectuate copy-protection. More specifically, the transient optical state change security materials may be used to manufacture optically readable digital storage medium that protects the information stored thereon from being copied using conventional optical medium readers, but permits reading of the information from the digital storage media by the same optical readers.

2. Description of the Related Art

Data is stored on optical media in the form of optical deformations or marks placed at discrete locations in one or more layers of the medium. Such deformations or marks effectuate changes in light reflectivity. To read the data on an optical medium, an optical medium player or reader is used. An optical medium player or reader conventionally shines a small spot of laser light, the "readout" spot, through the disc substrate onto the data layer containing such optical deformations or marks as the medium or laser head rotates. Two common types of optical media are the CD disc, providing a maximum storage space of about 650 megabytes of data on a single-side (SS), single-layer (SL) disc, and the DVD disc providing about 4.37 GB (1 GB=$2^{31}$ bytes) on a single-sided (SS), single-layer (SL) disc.

In conventional "read-only" type optical media (e.g., "CD-ROM"), data is generally encoded by a series of pits and lands that are metallized. A "readout" spot directed from the non-metallized side is reflected in a manner that the light of readout spot is reflected back into a photosensor in the reader. When referenced from the laser reading side, pits are technically referred to as bumps. The transitions between pits and lands, and the timing in between such transitions, represent channel bits. Thus the pit and lands in themselves are not representations of a sequence of zeros or ones. Typically, in CDs 14 channel bits make up a data symbol that translates to an 8 bit data value, in a process referred to as 8 to 14 modulation (EFM).

Microscopic pits formed in the surface of the plastic medium are arranged in tracks, conventionally spaced radially from the center hub in a spiral track originating at the medium center hub and ending toward the medium's outer rim. The pitted side of the medium is conventionally coated with a reflectance layer such as a thin layer of aluminum or gold. The "pits" as seen from the metallized side, are also referred to "bumps" when referencing view from the laser-read side. A lacquer layer is typically coated on the pit side as a protective layer.

The intensity of the light reflected from a read-only medium's surface measured by an optical medium player or reader varies according to the presence or absence of pits along the information track. When the readout spot is over a land, more light is reflected directly from the disc than when the readout spot is over a pit. As defect-induced errors may interfere with read, all optical discs employ error management strategies to eliminate the effect of such errors.

The optical reader, such as the CD or DVD reader, has the job of finding and reading the data stored as bumps on the CD. In a conventional player a drive motor spins the disc. A CD drive motor is designed to precisely control rotation of the disc between 200 and 500 rpm depending on which tract is being read. A laser and lens system focus light on the bumps, and an optical pickup receives reflected light. A tracking mechanism moves the laser assembly so that the laser's beam can follow the spiral track, conventionally moving the laser outward from the center as the CD is played. As the laser moves outward from the center of the disc, the bumps move past the laser faster, as the speed of the bumps is equal to the radius times the speed at which the disc is revolving (rpm). A spindle motor is conventionally employed to slow the speed of the CD when the laser is reading further and further out from the center of the disc permitting the laser to read at a constant speed, such that the data is read from the disc at a constant speed.

The semiconductor laser utilized, the spread of its wavelength, and its operational temperature affect the wavelength read by the pick up head (PUH) of the reader. DVD readers presently utilize lasers that produce a wavelength of about 630 to about 660 nm, with standard DVD readers measuring a wavelength of 650 ±5 nm and standard DVD-R readers measuring a wavelength of 650+10/−5 nm. CD readers presently utilize lasers that produce wavelengths between about 770 nm to about 830 nm, with standard CD readers having PUHs reading a wavelength of about 780 nm. As would be understood by one of skill in the art, the PUHs can detect only those reflected beams that fall within a certain angular deviation from the incident beam. For example, a typical DVD-R requires that the radial deviation be no more than ±0.80° and tangential deviation no more than ±0.30°.

The vast majority of commercially-available software, video, audio, and entertainment pieces available today are recorded in read-only optical format. One reason for this is that data replication onto read-only optical formats is significantly cheaper than data replication onto writable and rewritable optical formats. Another reason is that read-only formats are less problematical from a reading reliability standpoint. For example, some CD readers/players have trouble reading CD-R media, which has a lower reflectivity, and thus requires a higher-powered reading laser, or one that is better "tuned" to a specific wavelength.

Optical media of all types have greatly reduced the manufacturing costs involved in selling content such as software, video and audio works, and games, due to their small size and the relatively inexpensive amount of resources involved in their production. They have also unfortunately improved the economics of the pirate, and in some media, such as video and audio, have permitted significantly better pirated-copies to be sold to the general public than permitted with other data storage media. Media distributors report the loss of billions of dollars of potential sales due to high quality copies.

Typically, a pirate makes an optical master by extracting logic data from the optical medium, copying it onto a magnetic tape, and setting the tape on a mastering apparatus. Pirates also sometimes use CD or DVD recordable medium duplicator equipment to make copies of a distributed medium, which duplicated copies can be sold directly or used as pre-masters for creating a new glass master for replication. Hundreds of thousands of pirated optical media can be pressed from a single master with no degradation in the quality of the information stored on the optical media. As consumer demand for optical media remains high, and because such medium is easily reproduced at a low cost, counterfeiting has become prevalent.

WO 02/03386 A2, which asserts common inventors to the present application, discloses methods for preventing copying of data from an optical storage media by detecting optical dis-uniformities or changes on the disc, and/or changes in readout signal upon re-reading of a particular area on the optical storage medium, in particular those caused by light-sensitive materials, such as dyes, which may affect the readout wavelength by absorbing, reflecting, refracting or otherwise affecting the incident beam. Software control may be used to deny access to content if the dis-uniformity or change in read signal is not detected at the position on the disc wherein the dis-uniformity or change is anticipated. The disclosure of WO 02/03386 A2 is incorporated herein in its entirety by reference.

A preferred embodiment described in publication WO 02/03386 A2 comprises light-sensitive materials that are optical state change security materials that are positioned upon the optical disc in a manner that they do not adversely affect the data-read of the readout signal in one optical state, but upon exposure to the wavelength of the optical reader incident beam covert to a second optical state, preferably in a time-delayed fashion, does affect the data-read of the readout signal. In a preferred embodiment described in WO 02/03386 A2, the optical state change security material only transiently changes optical state and its optical state reverts over time.

There is a need for identifying optimal transient optical state change security materials that may be employed in a manner described in WO 02/03386 A2 to effectuate copy-protection of optical discs, in particular CDs and DVDs that conform to ISO/IEC standards when read by their respective ISO/IEC standardized readers. In particular there is a need for identifying materials that may be used in such copy protection methodologies that without requiring modification to optical medium readers.

DEFINITIONS

"Data Deformation": a structural perturbation on or in an item that represents stored data and can be read by an optical reader.

"Optical Medium": a medium of any geometric shape (not necessarily circular) that is capable of storing digital data that may be read by an optical reader.

"Optical Reader": a Reader (as defined below) for the reading of Optical Medium.

"Optical State Change Data Deformation": refers to an optical deformation on an item representative of data that is associated with an Optical State Change Security Material in such a manner that the data read of the deformation by an optical reader changes with the optical state of the Optical State Change Security Material.

"Optical State Change Security Material": refers to an inorganic or organic material used to authenticate, identify or protect an Optical Medium by changing optical state from a first optical state to a second optical state.

"Permanent Transient Optical State Change Security Material": refers to a Transient Optical State Change Security Material that undergoes change in optical state for more than thirty times upon read of the Optical Medium by an Optical Reader.

"Reader": any device capable of detecting data that has been recorded on an optical medium. By the term "reader" it is meant to include, without limitation, a player. Examples are CD and DVD readers.

"Read-only Optical Medium": an Optical Medium that has digital data represented in a series of pits and lands.

"Recording Layer": a section of an optical medium where the data is recorded for reading, playing or uploading to a computer. Such data may include software programs, software data, audio files and video files.

"Re-read": reading a portion of the data recorded on a medium after it has been initially read.

"Transient Optical State Change Security Material": refers to an inorganic or organic material used to authenticate, identify or protect an item by transiently changing optical state between a first optical state and a second optical state, and spontaneously reverting back to said first optical state after a period of time, and that may undergo such change in optical state more than one time upon read by an Optical Reader in a manner detectable by such Optical Reader.

"Transient Optical State Change Data Deformation": refers to an optical deformation on an item representative of data that is associated with a Transient Optical State Change Security Material in such a manner that the data read of the deformation by an optical reader changes with the optical state of the Transient Optical State Change Security Material.

"Temporary Transient Optical State Change Security Material": refers to a Transient Optical State Change Security Material that undergoes change in optical state for less than thirty times upon read of the Optical Medium by an Optical Reader.

For the purpose of the rest of the disclosure it is understood that the terms as defined above are intended whether such terms are in all initial cap, or not.

SUMMARY OF THE INVENTION

The present invention provides for a copy-protected optical medium which may be read by an optical reader, employing transient optical state change security materials prone to a measurable (as judged by the optical reader) optical phase change in the wavelength range of about 770 nm to about 830 nm comprising certain thiazine derivatives of the formula:

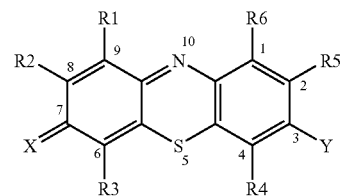

where R1 to R6 is hydrogen, alkyl, aryl, alkoxy, thioalkoxy, alkylamino, nitro, amino or halogen, and X and Y are either hydrogen, alkyl, aryl, alkoxy, thioalkoxy, alkylamino, nitro, amino and halogen, provided either of X or Y is a strong electron donating group to the thiazine backbone, and the other of X or Y is a strong electron withdrawing group with respect to the thiazine backbone.

BRIEF DESCRIPTION OF THE DRAWINGS

The accompanying drawings, which are incorporated in and constitute part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
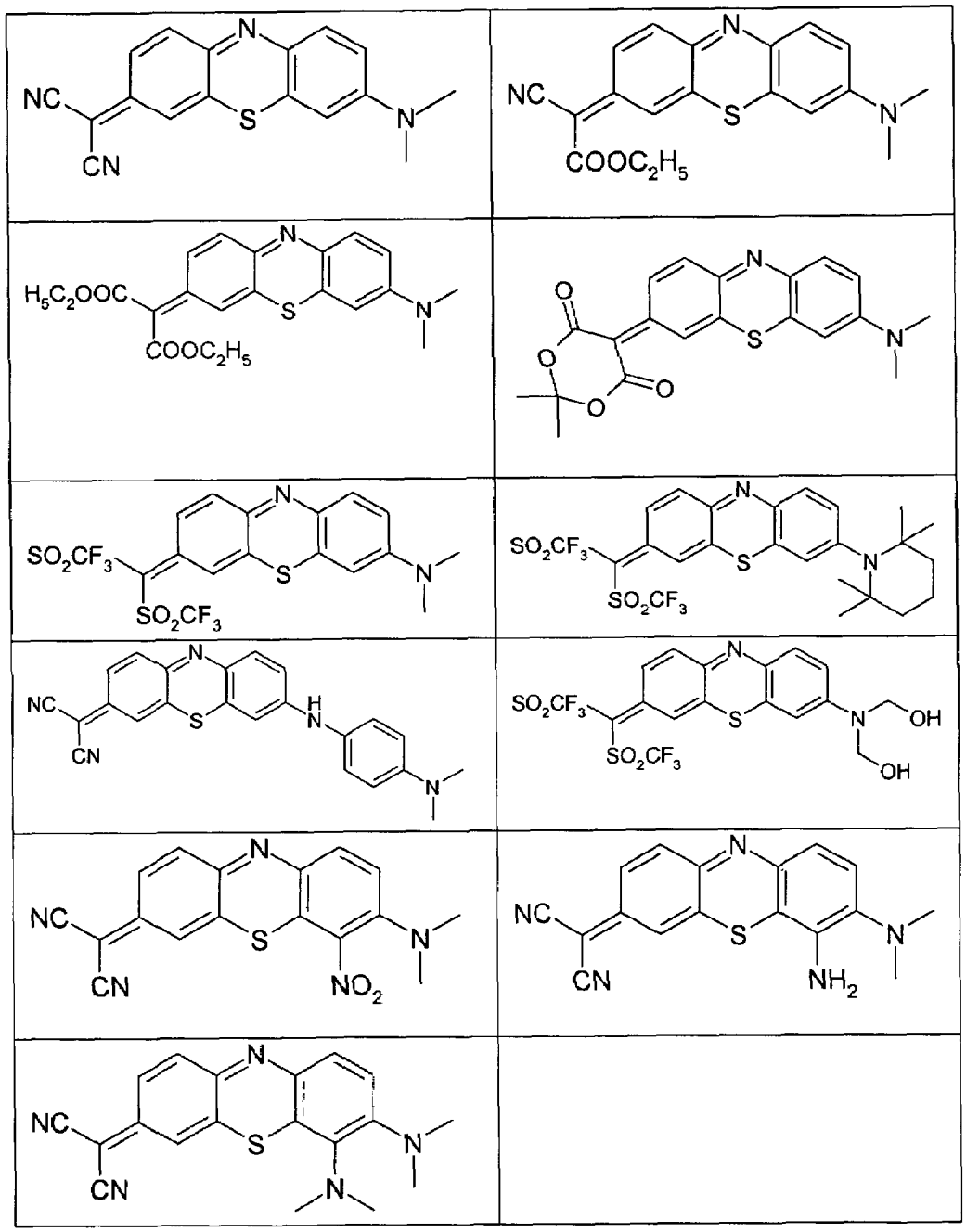
FIG. 1 illustrates thiazine compounds of the present invention that evince an optical state change when impinged upon by a wavelength of about 770 nm to about 830 nm.

The present invention provides for a copy-protected optical medium comprising transient optical state change security materials that may demonstrate an optical state change when exposed to the wavelengths of a typical CD optical reader, that is, about 770 nm to about 830 nm.

It has been found that certain "push-pull" types of thiazine dyes of the general structural formula:

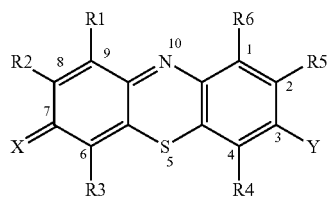

where R1 to R6 is hydrogen, alkyl, aryl, alkoxy, thioalkoxy, alkylamino, nitro, amino or halogen, and X and Y are either hydrogen, alkyl, aryl, alkoxy, thioalkoxy, alkylamino, nitro, amino and halogen, provided either of X or Y is a strong electron donating group to the thiazine backbone, and the other of X or Y is a strong electron withdrawing group with respect to the thiazine backbone, may evince an optical state change that is detectable by an optical reader operating in the wavelengths of about 770 nm to about 830 nm.

By attaching strong electron donating and electron withdrawing groups at the 3 and 7 positions, a push-pull structure may be obtained. This kind of structure has a significant bathochromic shift compared with methylene blue.

PREPARATION OF EXEMPLAR "PUSH-PULL" THIAZINE COMPOUNDS

EXAMPLE 1

Phenothizine5-ium Tretraiodide Hydrate

A solution of phenothiazine (2.13 g, 11 mmoles) in chloroform (75 ml) was stirred at 5° C. and treated dropwise within 1 hour with a solution of iodine (8.38 g, 66 mmoles) in chloroform (175 ml). The mixture was stirred at 5° C. for an additional 30 minutes and the resultant precipitate was filtered, washed with chloroform, and then kept at vacuum at room temperature until the weight is constant. Afforded a black powder, 7.10 g (90%).

EXAMPLE 2

3-(Dimethylamino)phenothiazine-5-ium Triiodide

A solution of phenothiazine-5-ium tetraiodide hydrate (0.417 g, 0.57 mmol) in methanol (10 ml) was stirred at room temperature and treated dropwise with a solution of dimethylamine (1.14 mmole) in methanol (2 ml). The mixture was stirred at room temperature for 3 hrs until the starting materials was consumed, as monitored by TLC (silica, CH$_3$OH/TEA). The precipitate was filtered and washed with small amount of methanol, afforded a black solid, 0.30 g (84%).

EXAMPLE 3

[7-(Dimethylamino)phenothiazine-3-ylidene]methane-1,1-dicarbonitrile

To the solution of 3-(dimethylamino)phenothiazine-5-ium triiodide (0.15 g, 0.24 mmole) in methanol (10 ml) was added malononitrile (0.095 g, 1.44 mmole) and sodium carbonate (0.28 g, 2.88 mmole), and the mixture was stirred at room temperature for 2 hrs, and the reaction was monitored by UV-Vis. Then brine and CH$_2$Cl$_2$ were added to the reaction mixture, and the CH$_2$Cl$_2$ layer was separated, washed with water, brine and dried (Na$_2$SO$_4$). Purification by column chromatography (SiO$_2$, CH$_2$Cl$_2$) afforded a deep blue band, and after removal of the solvent, afforded a purple solid.

Other exemplar thiazine compounds of the present invention are set forth in FIG. 1.

STATEMENT REGARDING PREFERRED EMBODIMENTS

While the invention has been described with respect to preferred embodiments, those skilled in the art will readily appreciate that various changes and/or modifications can be made to the invention without departing from the spirit or scope of the invention as defined by the appended claims. All documents cited herein are incorporated in their entirety herein.

The invention claimed is:

1. A copy protected optical disc having associated therewith having one or more compounds selected from the group consisting of:

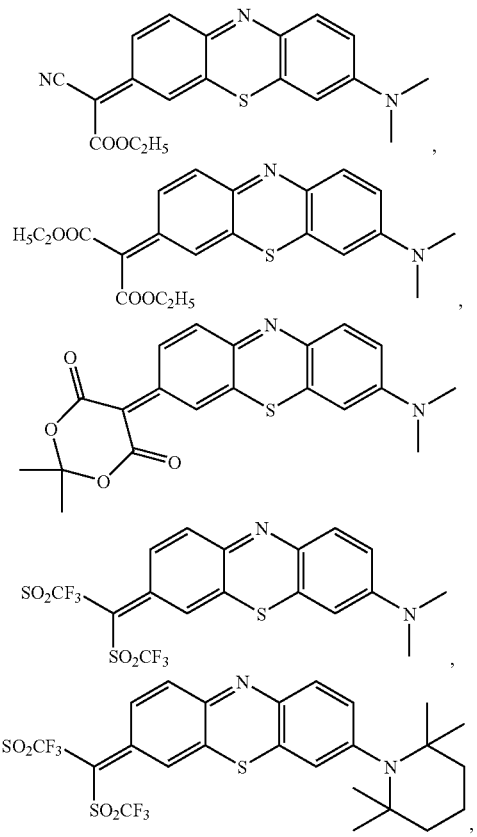

-continued

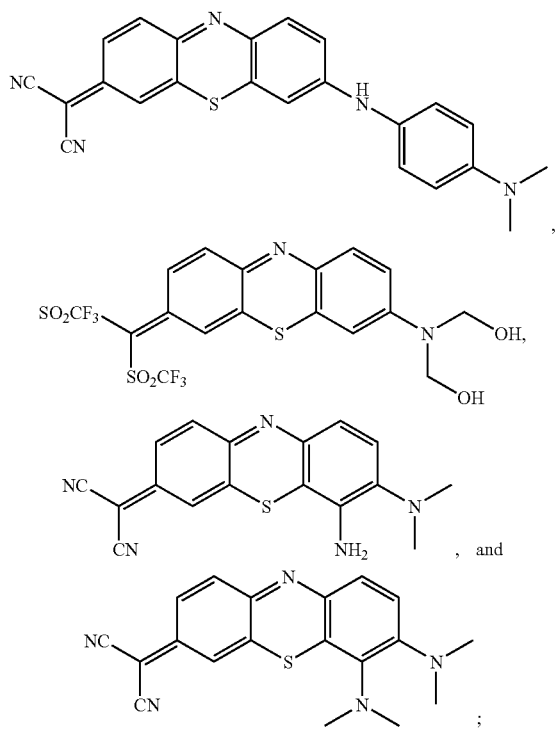

wherein said compound is detectable on said optical disc by an optical reader producing a defined wavelength of from about 770 mn to about 830 nm due to change in optical state from an initial optical state to a second optical state.

2. A copy-protected optical disc of claim 1 wherein compound(s) are associated with an optical data deformation in a manner such that the read of the optical data deformation is different when the compound(s) are in their initial optical state and their second optical state.

3. A copy-protected optical disc of claim 1 wherein at least one of the compound(s) capable of optical phase change comprises: [7(Dimethylamino)phenothiazine-3-ylidene]methane-1,1-dicarbonitrile.

4. A copy-protected optical disc having associated therewith a layer comprising phenothiazine-5-ium tetraiodide hydrate wherein such compound is detectable on said optical disc by an optical reader producing a defined wavelength of from about 770 nm to about 830 nm due to change in optical state from an initial optical state to a second optical state.

5. A copy protected optical disc having associated therewith a layer comprising 3-(Dimethylamino)phenothiazine-5-ium Triiodide wherein such compound is detectable on said optical disc by an optical reader producing a defined wavelength of from about 770 nm to about 830 nm due to change in optical state from an initial optical state to a second optical state.

* * * * *